United States Patent [19]

Borrevang et al.

[11] Patent Number: 5,262,430

[45] Date of Patent: Nov. 16, 1993

[54] SUBSTITUTED 2-IMIDAZOLINES AND USE THEREOF

[75] Inventors: Poul Borrevang; Henrik S. Andersen, both of Copenhagen, Denmark

[73] Assignee: Novo Nordisk A/S, Bagsvaerd, Denmark

[21] Appl. No.: 781,269

[22] PCT Filed: Jul. 12, 1990

[86] PCT No.: PCT/DK90/00184
§ 371 Date: Dec. 16, 1991
§ 102(e) Date: Dec. 16, 1991

[87] PCT Pub. No.: WO91/00862
PCT Pub. Date: Jan. 24, 1991

[30] Foreign Application Priority Data

Jul. 12, 1989 [DK] Denmark .............................. 3444/89

[51] Int. Cl.$^5$ .................... A61K 31/44; A61K 31/415; C07D 401/14; C07D 405/06
[52] U.S. Cl. ...................................... 514/337; 514/402; 548/311.4; 546/269
[58] Field of Search ............................ 548/348, 311.4; 514/402, 337; 546/269

[56] References Cited

U.S. PATENT DOCUMENTS 4,138,491  2/1979  Ishikawa et al. .................... 548/348

FOREIGN PATENT DOCUMENTS 0071368  2/1983  European Pat. Off. ............ 548/348
2167408  5/1986  United Kingdom .

OTHER PUBLICATIONS

Areschka et al., Chim. Ther., No. 4, pp. 337–344 (1972).

*Primary Examiner*—Patricia L. Morris
*Attorney, Agent, or Firm*—Steve T. Zelson; Cheryl H. Agris

[57] ABSTRACT

The invention relates to novel substituted 2-imidazolines (I) having a lowering effect on blood glucose in mammals, to their preparation, to pharmaceutical compostions containing them and to their use.

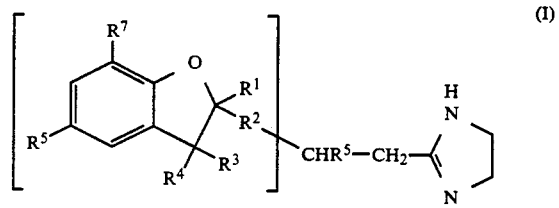

18 Claims, No Drawings

SUBSTITUTED 2-IMIDAZOLINES AND USE THEREOF

This application claims the benefit of copending PCT Application No. PCT/DK90/00184, filed Jul. 12, 1990, designating the United States of America.

FIELD OF THE INVENTION

The present invention relates to novel substituted 2-imidazolines having a lowering effect on blood glucose in mammals, to their preparation, to pharmaceutical compositions containing them and to their use.

BACKGROUND OF THE INVENTION

Diabetes mellitus is a widespread disease, and the diagnosis is based upon elevated blood glucose levels.

There are at least two subtypes of the disease: type 1 or insulin dependent diabetes mellitus, and type 2 non insulin dependent diabetes mellitus. Worldwide the number of diabetics is steadily increasing, especially in the group with type 2 diabetes, where up to 10% of the older generation (>65 years of age) in the western hemisphere will suffer from type 2 diabetes.

The separation of the two subclasses is based on pathophysiological and clinical findings. In type 1 diabetes the insulin producing $\beta$-cells in pancreas are destroyed by a selective auto immune reaction. The clinical outcome is due to the absolute insulin deficiency, and these patients will die from the disease unless treated with insulin regularly.

The underlying pathophysiological mechanisms in type 2 diabetes are not fully clarified. The various tissues are less sensitive to insulin (insulin resistance). The $\beta$-cell function is partially preserved, and the type 2 diabetic patients secrete enough insulin to be protected from the development of diabetic coma—eventually leading to exitus.

However, the insulin secretion pattern is altered in connection with meals, as the increase is too slow and protracted and unable to normalize the blood glucose profile. In more severe cases the $\beta$-cell function is also decreased in the fasting state, and fasting blood glucose becomes elevated as well. The normal, complex regulation of the $\beta$-cell function is disturbed in type 2 patients. This regulation include the effect of different substrates (e.g. glucose, alanine), and hormones (e.g. glucagon), which may increase or decrease the insulin release. Furthermore the secretion is also regulated via $\alpha$- and $\beta$-adrenergic nerve fibres. It is striking that especially glucose becomes less effective as an insulin-releasing agent in type 2 diabetics as the disease becomes more severe.

According to current recommendations all type 2 patients are prescribed a diabetes diet, and some patients achieve acceptable blood glucose levels on diet alone. However, the majority of patients needs some kind of medical treatment as well. The standard approach is to prescribe a sulphonylurea, which will cause an increase in insulin secretion. Sulphonylureas are effective even at normal or low levels of blood glucose. Therefore there is a considerable risk of the occurence of severe hypoglycaemia on sulphonylurea treatment, and even fatal cases have been reported.

Good glycaemic control (i.e. constant blood glucose values near normal levels) is officially recommended as the only way to protect patients from the diabetic micro- and macro-vascular complications, such as blindness, renal failure, acute myocardial infarction, gangrene, etc. However, many patients are reluctant to follow this strategy, as they anticipate a higher number of severe hypoglycaemic attacks.

DESCRIPTION OF THE PRIOR ART

A method for treating diabetes comprising administering a therapeutically effective amount of 2-[2-phenyl-2-(2-pyridyl)]ethyl-2-imidazoline is described in U.S. Pat. No. 4,138,491 (Daiichi Seiyaku Co., Ltd.). However the Daiichi patent contains no mention of a moderate effect of the compounds when the blood glucose is low and a stronger effect when the blood glucose is high.

Imidazoline derivatives wherein the 2-position of an otherwise unsubstituted 2-imidazoline nucleus is linked to the 2-position of an optionally substituted 2,3-dihydrobenzofuran are described in European patent application publication No. 71,368 (Reckitt and Colman Products, Ltd.). The compounds exhibit presynaptic $\alpha_2$-adrenoreceptor antagonist activity, and in the specification it is mentioned that $\alpha_2$-adrenoreceptor antagonists may have a role to play in the control of diabetes. However, the application has no claims directed to this use and no experimental results concerning this aspect are presented.

GB patent application publication No. 2,167,408 (Farmos Yhtyma OY) describes selective $\alpha_2$ receptor antagonists. The compounds comprise an otherwise unsubstituted imidazole ring which through its 4(5)-position is linked to a ring carbon atom in an optionally substituted ring system. In the application it is mentioned that $\alpha_2$ receptor antagonists may be useful in the treatment of diabetes. However, the application contains no experimental results or claims relating to this indication.

The present standard treatment of type 2 diabetes is far from optimal. The majority of the type 2 diabetic patients are not well controlled, which is demonstrated by the very high number of patients with severe diabetic complications. Therefore new ways of treatment are urgently needed.

SCOPE OF THE INVENTION

According to the present invention there are provided novel compounds with a lowering effect on blood glucose in mammals including man.

The compounds according to the present invention are expected to represent a major improvement of the present treatment of type 2 diabetes, the predominant features of these novel compounds being:
1. A strong ability to decrease blood glucose when the initial level is high e.g. in connection with meals.
2. A much more subtle effect on blood glucose in the fasting state (relative inability to induce hypoglycaemia).

Thus it can be expected that the compounds of the invention will enable the patient to achieve a good glycaemic control while at the same time the risk of hypoglycaemic attacks is minimized.

SUMMARY OF THE INVENTION

In its broadest aspect the present invention comprises 2-imidazolines which via a two-linked carbon chain in the 2-position are linked to the 2-, 5-, or 7-position of an optionally substituted benzofuran ring which may be partly saturated. The compounds according to the present invention thus have the general formula (I):

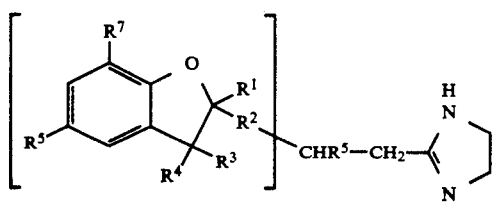

wherein $R^1$ is hydrogen, fluoro, chloro, bromo, $C_{1-4}$alkyl, $C_{1-4}$alkoxy or a bond to the side chain carrying the imidazoline ring; $R^2$ is hydrogen, fluoro, chloro, bromo, $C_{1-4}$alkyl, $C_{1-4}$alkoxy or together with $R^3$ represents an additional bond; $R^3$ is hydrogen, $C_{1-4}$alkyl, $C_{1-4}$alkoxy, fluoro, chloro or bromo, phenyl, phenyl substituted by a substituent selected from the group consisting of fluoro, and chloro, $C_{1-4}$alkyl (e.g. methyl), $C_{1-4}$alkoxy (e.g. methoxy) or together with $R^2$ represents an additional bond; $R^4$ is hydrogen, $C_{1-4}$alkyl, $C_{1-4}$alkoxy, fluoro, chloro, bromo, phenyl, phenyl substituted by a substituent selected from the group consisting of fluoro, and chloro, $C_{1-4}$alkyl (e.g. methyl), $C_{1-4}$alkoxy (e.g. methoxy); $R^5$ is hydrogen, fluoro, chloro, bromo, $C_{1-4}$alkyl, $C_{1-4}$alkoxy, hydroxy, phenyl optionally substituted by methyl, methoxy, fluoro or chloro, or a bond to the side chain carrying the imidazoline ring; $R^6$ is phenyl optionally substituted by methyl, methoxy, fluoro or chloro, 2-pyridyl, 3-pyridyl or 4-pyridyl, preferably 2-pyridyl, each pyridyl group optionally carrying a $C_{1-4}$alkyl substituent (preferably methyl); $R^7$ is hydrogen, fluoro, chloro, bromo, $C_{1-4}$alkyl, $C_{1-4}$alkoxy, hydroxy, phenyl, optionally substituted by methyl, methoxy, fluoro, chloro or $R^7$ is a bond to the side chain carrying the imidazoline ring. When $R^2$ and $R^3$ do not together represent an additional bond and $R^1$ and $R^2$ are different from each other and/or $R^4$ and $R^3$ are different from each other the compounds of formula (I) exist in stereoisomeric or diastereoisomeric forms. The carbon atom to which $R^6$ is linked is assymmetric thus giving rise to optical isomers. All these isomeric forms and mixtures thereof are within the scope of the invention as are the pharmaceutically acceptable acid addition salts of the compounds of formula (I).

In a first group of preferred compounds according to the invention $R^1$ is a bond to the side chain carrying the imidazoline ring.

In a second group of preferred compounds according to the invention $R^1$ is hydrogen, fluoro, chloro, bromo, $C_{1-4}$alkyl, or $C_{1-4}$alkoxy, more preferred $R^1$ is hydrogen or $C_{1-4}$alkyl.

In a further group of preferred compounds according to the invention $R^2$ together with $R^3$ represents an additional bond.

In a further group of preferred compounds according to the invention $R^2$ is hydrogen, fluoro, chloro, bromo, $C_{1-4}$alkyl, or $C_{1-4}$alkoxy, more preferred $R^2$ is hydrogen or $C_{1-4}$alkyl.

In a further group of preferred compounds according to the invention $R^3$ is hydrogen, fluoro, chloro, bromo, $C_{1-4}$alkyl, $C_{1-4}$alkoxy, phenyl optionally substituted by a substituent selected from the group consisting of fluoro, chloro, $C_{1-4}$alkyl (e.g. methyl), and $C_{1-4}$alkoxy (e.g. methoxy), more preferred $R^3$ is hydrogen or $C_{1-4}$alkyl.

In a further group of preferred compounds according to the invention $R^4$ is hydrogen, $C_{1-4}$alkyl, $C_{1-4}$alkoxy, fluoro, chloro, bromo, phenyl optionally substituted by a substituent selected from the group consisting of fluoro, chloro, $C_{1-4}$alkyl (e.g. methyl), and $C_{1-4}$alkoxy (e.g. methoxy), more preferred $R^4$ is hydrogen or $C_{1-4}$alkyl.

In a further group of preferred compounds according to the invention $R^5$ is a bond to the side chain carrying the imidazoline ring.

In a further group of preferred compounds according to the invention $R^5$ is hydrogen, fluoro, chloro, bromo, $C_{1-4}$alkyl, $C_{1-4}$alkoxy, hydroxy, or phenyl optionally substituted by a substituent selected from the group consisting of methyl, methoxy, fluoro or chloro, more preferred $R^5$ is hydrogen, fluoro, chloro, bromo, $C_{1-4}$alkyl, or $C_{1-4}$alkoxy.

In a further group of preferred compounds according to the invention $R^6$ is phenyl optionally substituted by methyl, fluoro or chloro.

In a further group of preferred compounds according to the invention $R^6$ is 2-pyridyl, 3-pyridyl or 4-pyridyl, preferably 2-pyridyl.

In a further group of preferred compounds according to the invention $R^6$ is 2-pyridyl, 3-pyridyl or 4-pyridyl, in each case substituted by a $C_{1-4}$alkyl substituent, preferably methyl.

In a further group of preferred compounds according to the invention $R^7$ is a bond to the side chain carrying the imidazoline ring.

In a further group of preferred compounds according to the invention $R^7$ is hydrogen, fluoro, chloro, bromo, $C_{1-4}$alkyl, $C_{1-4}$alkoxy, hydroxy, or phenyl optionally substituted by a substituent selected from the group consisting of methyl, methoxy, fluoro, or chloro, more preferred $R^7$ is hydrogen, fluoro, chloro, bromo, $C_{1-4}$alkyl, or $C_{1-4}$alkoxy.

The compounds of the present invention can be prepared according to the methods outlined in the following description of preparation methods A-F.

DESCRIPTION OF THE PRESENTLY PREFERRED EMBODIMENTS

Preparation Method A

The compounds of the formula (II) of the present invention are prepared as outlined in scheme A.

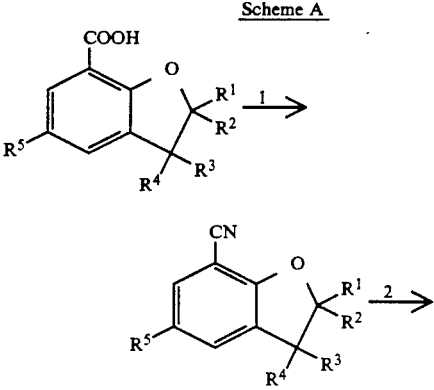

-continued
Scheme A

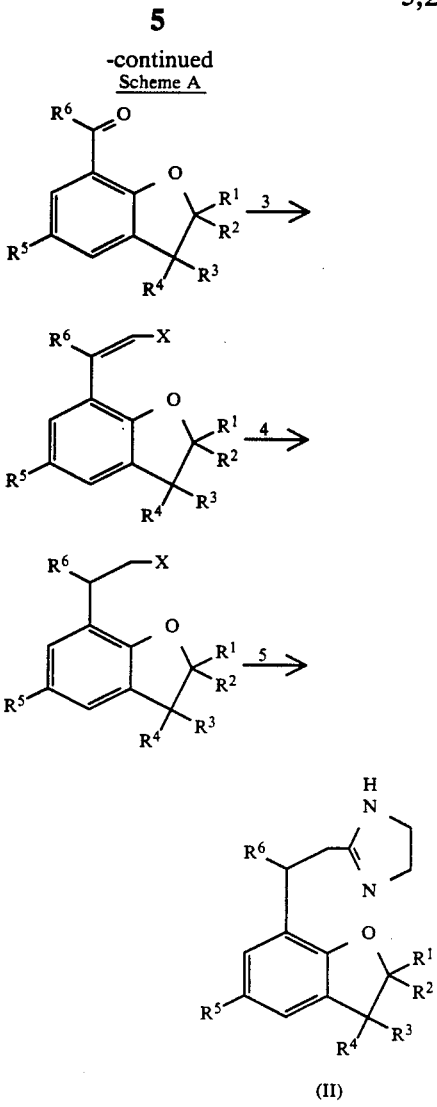

(II)

X = COOR$^7$, R$^7$ is alkyl, phenyl or benzyl.

Step 1. A substituted 7-benzofuran carboxylic acid wherein R$^1$,R$^2$,R$^3$,R$^4$ and R$^5$ are as defined above (R$^1$ and R$^5$ are not a bond to the side chain carrying the imidazoline ring) is transformed into the corresponding nitrile. First, the acid is transformed into an acid chloride by known methods. While an inert solvent may be employed it is generally preferred to use an excess of the chlorinating agent as a solvent in order to dispense with the use of further solvents.

Generally the reaction mixture is heated to at least 60° C. The acid chloride is transformed into the corresponding amide by reacting it with a ammonium hydroxide solution. The amide is isolated using known techniques.

In order to form the nitrile the amide is reacted with a dehydrating agent such as oxalyl chloride or thionyl chloride. Generally the reaction mixture is heated to at least 70° C. for 1 hour and later to 90° C. for 4 to 18 hours. The nitrile is isolated using known techniques and recrystallized from an alcohol (methanol, ethanol, propanol, 2-propanol, tert-butanol).

Step 2. The substituted 7-cyano-benzofuran from Step 1 is transformed into the ketone wherein R$^1$,R$^2$,R$^3$,R$^4$,R$^5$ and R$^6$ are as defined above. In this step the nitrile is reacted with 2-lithium pyridin to form a imine which is hydrolysed with an acid to the corresponding ketone. The ketone is isolated using known techniques and recrystallized (if a solid) from an alcohol (methanol, ethanol, 2-propanol or tert-butanol). In an alternative method wherein R$^1$,R$^2$,R$^3$,R$^4$ and R$^5$ are as defined above the nitrile is reacted with a Grignard reagent to form a imine which is hydrolysed to the corresponding ketone. The Grignard reagent is prepared by known methods.

Step 3. The 3,3-disubstituted acrylic acid derivatives wherein R$^1$,R$^2$,R$^3$,R$^4$,R$^5$ and R$^6$ are as defined above, are prepared from the ketones by reacting them with the corresponding disubstituted phosphonoacetic acid derivatives (X and R$^7$ as defined above) under Webb's modified Wittig-Horner condition (Webb et al. synthesis 122 (1974)). The reaction is carried out at from −10° C. to the reflux temperature of the reaction mixture and is generally complete in from 3 to 24 hours. It is preferred to carry out the reaction at from about room temperature to 40° C. The product is isolated using techniques known to those skilled in the art with the product generally not being purified but rather used directly in the next step.

Step 4. The olefinic products serve as intermediates for preparation of the corresponding reduced 3,3-disubstituted propionic acid derivatives wherein R$^1$,R$^2$,R$^3$,R$^4$,R$^5$,R$^6$,X and R$^7$ are as defined above. While the reduction of the above olefinic compounds can be carried out by employing a number of reducing agents which are known to reduce carbon-to-carbon double bonds, the preferred methods employ hydrogen in the presence of a nobel metal catalyst (e.g. palladium on carbon) or sodium amalgam in an suitable solvent. An especially preferred solvent is ethanol. Hydrogen at from 1 to 4 atmospheres is employed and the reaction is complete in from 4 to 24 hours. Room temperature is preferred, however, an elevated temperature of up to 50° C. may be employed. The product is isolated using standard techniques. If desired, purification is done by well known methods such as crystallization or by chromatography.

Step 5. The propionic acid derivatives are used to prepare the corresponding 2-imidazolines (II) wherein R$^1$,R$^2$,R$^3$,R$^4$,R$^5$,R$^6$ and R$^7$ are as defined above. Conventional preparation of 2-imidazolines normally requires nitriles or imino ethers as starting materials. Only in selected cases can carboxylic acid ester be reacted directly with ethylenediamine to give 2-imidazolines. Drastic reaction conditions (sealed tube, 160°-300° C. and Mg as an catalyst) often limit the usefulness of these procedures. A bifunctional unit such as 1,2-diaminoethane is effectively coupled with trimethylaluminum to produce reagents that are treated with a carboxylic acid ester to give 2-imidazolines. The reaction is carried out at from −10° to 0° C. The carboxylic acid ester is normally added dissolved in the solvent of choice. The reaction is carried out at reflux temperature of the reaction mixture and is generally compleat in from 4 to 12 hours. The product is isolated using techniques known to those skilled in the art with the product generally being purified by well known methods such as crystallization and/or chromatography.

Preparation Method B

The compounds of the formula (III) of the present invention are prepared as outlined in scheme B.

Scheme B

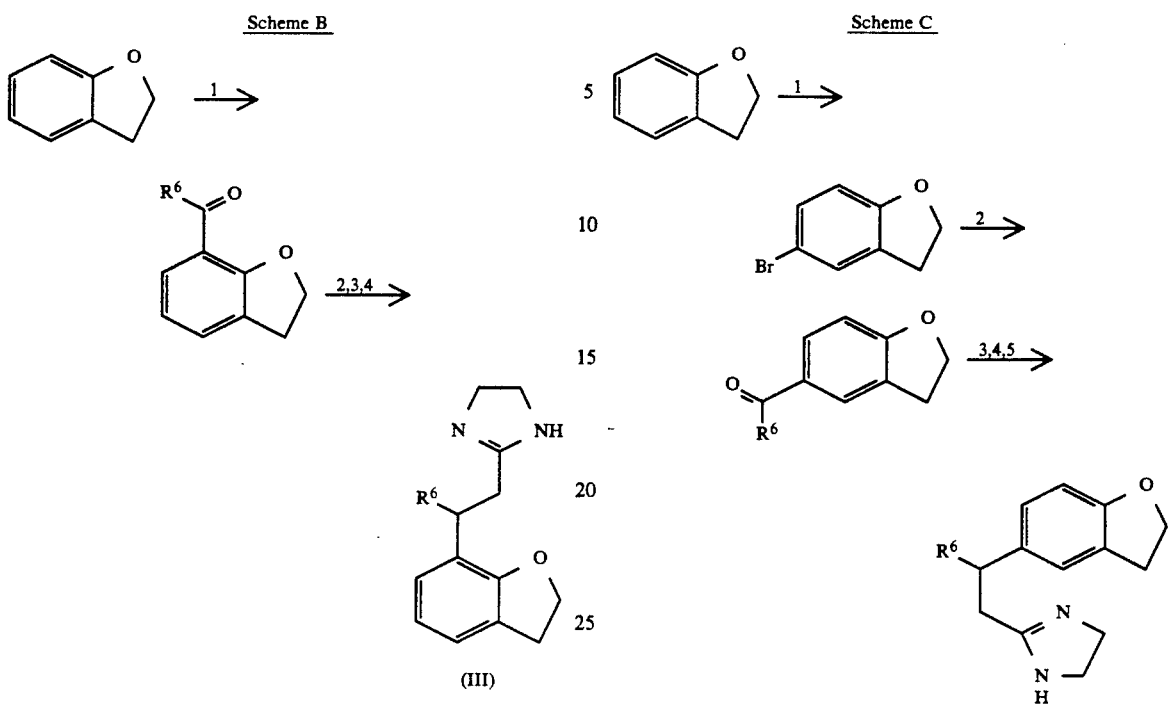

Step 1. 2,3-Dihydrobenzofuran is transformed into the ketone wherein $R^6$ is as defined above. In this step 2,3-dihydrobenzofuran is treated with a lithium base to form 2,3-dihydro-7-lithium-benzofuran which is reacted with a 2-cyano pyridine to form a imine which is hydrolysed with an acid to the corresponding ketone. Temperature is not very critical, but will generally be from $-5°$ C. to the reflux temperature of the reaction mixture. To the lithium reagent, at the temperature interval mentioned, is added the nitrile mentioned above. The imine is hydrolysed to the ketone by known methods. The ketone is isolated using known techniques and recrystallized from an alcohol (methanol, ethanol, 2-propanol, tert-butanol).

Step 2. As Step 3 in preparation method A. $R^1, R^2, R^3, R^4, R^5$ are H.

Step 3. As Step 4 in preparation method A. $R^1, R^2, R^3, R^4, R^5$ are H.

Step 4. As Step 5 in preparation method A. $R^1, R^2, R^3, R^4, R^5$ are H.

Preparation Method C

The compounds of the formula (IV) of the present invention are prepared as outlined in scheme C.

Step 1. Bromination of 2,3-Dihydrobenzofuran gives 5-bromo-2,3-dihydrobenzofuran which serves as an intermediate for the ketone in scheme C step 2. Bromination of 2,3-dihydrobenzofuran is performed by conventional means. 2,3-dihydrobenzofuran is normally brominated by adding 1 equivalent of bromine to a solution of 2,3-dihydrobenzofuran in an appropriate solvent. The reaction is carried out at from 0° C. to 25° C. and is generally complete in 3 hours. The product is isolated using techniques known to those skilled in the art. Purification, if desired, is performed by distillation.

Step 2. 5-Bromo-2,3-dihydro-benzofuran is transformed into the ketone wherein $R^6$ is as defined above. In this step a cyano pyridine is reacted with 2,3-dihydrobenzofuran-5-magnesium-bromide to form an imine which is hydrolysed to the corresponding ketone. The Grignard reagent is prepared by known methods. The imine is hydrolysed to the ketone by known methods. The ketone is isolated using known techniques and recrystallized (if solid) from an alcohol (methanol, ethanol, 2-propanol, tert-butanol).

Step 3. As Step 3 in preparation method A. $R^1, R^2, R^3, R^4, R^7$ are H.

Step 4. As Step 4 in preparation method A. $R^1, R^2, R^3, R^4, R^7$ are H.

Step 5. As Step 5 in preparation method A. $R^1, R^2, R^3, R^4, R^7$ are H

Preparation Method D

The compounds of the formula (V) of the present invention are prepared as outlined in scheme D.

Starting material (Formula D) for preparation of the compounds of the formula (V), wherein the imidazoline side chain is positioned in position 2 of the benzofuran nucleus, is described in literature (F. Binon et al., Chimie Therapeutique 2, 113 (1967) and J. Chem. Soc. 3693 (1955)).

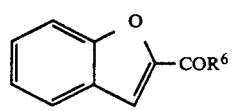

Formula D

When $R^6$ is as defined above the benzofuran nucleus can be substituted in various positions with halogen (chlorine, bromine), alkyl (preferably methyl) and alkyloxy (preferably methoxy).

Scheme D

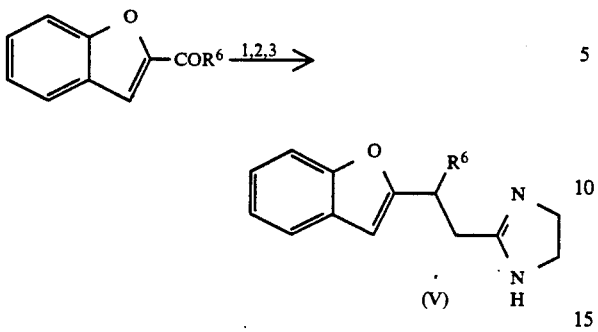

Step 1. As Step 3 in preparation method A.
Step 2. As Step 4 in preparation method A.
Step 3. As Step 5 in preparation method A.

Preparation Method E

The compounds of the formula (VI) of the present invention are prepared as outline in scheme E.

Step 1. An appropriate 5-halogen benzofuran, (preferably 5-chloro-benzofuran) is transformed into the corresponding 7-bromo-5-halogen-2,3-dihydrobenzofuran wherein $R^6$ is as defined above and $R^5$ is halogen (fluoro, chloro or bromo). In this step, selective reduction of the 2,3-double bond in the benzofuran nucleus gives 2,3-dihydrobenzofurans which by selective bromination give 7-bromo-5-halogen-2,3-dihydrobenzofuran. While reduction of 5-halogen-benzofuran can be carried out by employing a number of reducing agents which are known to reduce carbon-to-carbon double bonds, the preferred methods employ hydrogen in the presence of a nobel metal catalyst (preferably rhodium on carbon). When the reduction is carried out employing hydrogen in the presence of a nobel metal catalyst, a convenient method for carrying out this transformation is to stir or shake a solution of the 5-halogen-benzofuran compound under an atmosphere of hydrogen, in the presence of a noble metal hydrogenation catalyst. Suitable solvents for this reaction are those which substantially dissolve the starting compound but which do not themselves suffer hydrogenation or hydrogenolysis. Examples of such solvents include alcohols such as methanol and ethanol and the like; ethers such as diethyl ether, tetrahydrofuran and the like. An especially preferred solvent is ethanol. Room temperature is preferred, however, an elevated temperature of up to 50° C. may be employed. The product is isolated using standard techniques.

Scheme E

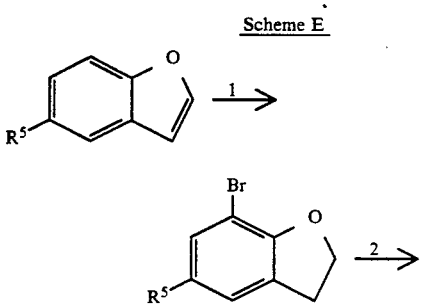

-continued
Scheme E

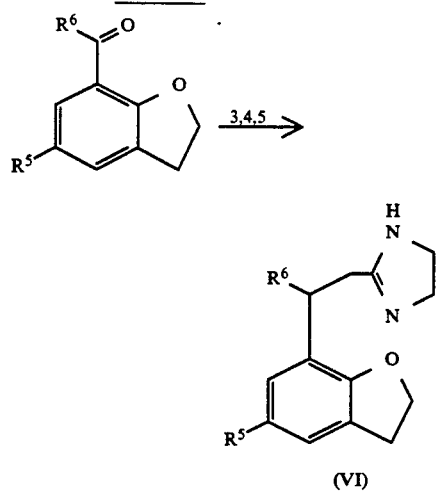

If desired, purification is performed by well known methods such as crystallization or chromatography.

5-halogen-2,3-dihydrobenzofuran is brominated to yield 7-bromo-5-halogen-2,3-dihydrobenzofuran as described in preparation method C step 1. The product is isolated using standard techniques. If desired, purification is performed by well known methods such as distillation or crystallization.

Step 2. 7-bromo-5-halogen-2,3-dihydro-benzofuran is transformed into a ketone wherein $R^5$ and $R^6$ are as defined above. In this step a cyano pyridine is reacted with 5-halogen-2,3-dihydrobenzofuran-7-magnesium-bromide to form an imine which is hydroysed to the corresponding ketone. The Grignard reagent is prepared by known methods.

In an alternative method wherein $R^5$ and $R^6$ are as defined above 7-bromo-5-halogen-2,3-dihydrobenzofuran is treated with a lithium base to form 5-halogen-2,3-dihydro-7-lithium-benzofuran which is reacted with a cyano pyridine to form an imine which is hydrolysed with an acid to give the corresponding ketone. The imine is hydrolysed to the ketone by known methods. The ketone is isolated using known techniques and recrystallized (if solid) from an alcohol (methanol, ethanol, propanol, 2-propanol or tert-butanol), preferably ethanol.

Step 3. As Step 3 in preparation method A. $R^1, R^2, R^3$ and $R^4$ are H.

Step 4. As Step 4 in preparation method A. Preferred is a nobel metal catalyst such as rhodium on carbon. $R^1, R^2, R^3$ and $R^4$ are H.

Step 5. As Step 5 in preparation method A. $R^1, R^2, R^3$ and $R^4$ are H.

Preparation Method F

The compounds of the formula (VII) of the present invention are prepared as outlined in scheme F.

Scheme F

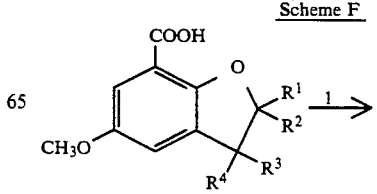

-continued
Scheme F

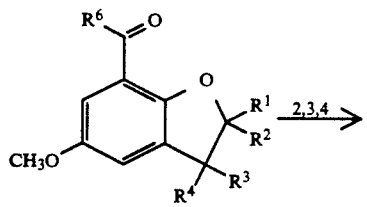

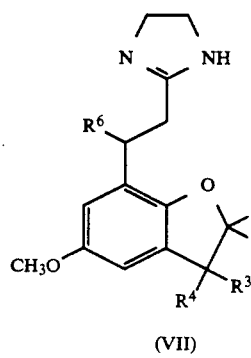

(VII)

Step 1. An appropriately substituted 5-methoxybenzofuran-7-carboxylic acid is transformed into the ketone wherein R, $R^2, R^3, R^4$ and $R^6$ are as defined above with the proviso that $R^1$ cannot be a bond to the side chain carrying the imidazoline ring. In the first step, the acid is transformed into an acid chloride by reaction with a chlorinating agent such as phosphorus oxychloride or thionyl chloride. The 5-methoxybenzofuran-7-carbonyl chloride wherein $R^1, R^2, R^3, R^4$ and $R^6$ are as defined above is reacted with 2-trimethylsilyl pyridine to form a ketone. The solvent employed is generally a solvent compatible with the reaction condition and it is thus generally preferred to use dimethyl formamide. It is generally preferred to add a base in order to speed up the reaction and preferred as a base is a sterically hindered alkoxide base such as potassium tert-butoxide. Room temperature is preferred, however, an elevated temperature of up to 50° C. may be employed.

In an alternative method wherein $R^6$ is as defined above the 5-methoxybenzofuran-7-carbonyl chloride is transformed by known methods into the corresponding symmetric anhydride which is reacted with 2-trimethylsilyl pyridine to form the ketone as described above. An elevated temperature of up to 100° C. may be employed. The ketone is isolated using known techniques and recrystallized (if solid) from an alcohol (methanol, ethanol, 2-propanol or tert-butanol), preferably ethanol.

Step 2. As Step 3 in preparation method A. $R^1, R^2, R^3, R^4$ as defined above, $R^5$ is methoxy.

Step 3. As Step 4 in preparation method A. $R^1, R^2, R^3, R^4$ as defined above, $R^5$ is methoxy.

Step 4. As Step 5 in preparation method A. $R^1, R^2, R^3, R^4$ as defined above, $R^5$ is methoxy.

Pharmacological Test Results

The compounds were tested in 200–250 g male Wistar rats, which were either fed or fasted overnight. The animals were anaesthesized with a barbital injection i.p. and a catheter was placed in the internal carotid artery. The animals received either a 10 mg/kg i.v. injection of one of the compounds of the invention or a control injection of saline.

The findings are summarized in table 1 and 2 and expressed as mean values.

Table 1

| Min. after adm. | Blood glucose (mmol/l) after administration of compound (7), (27), and (32) to normal rats | | | | | | control fed |
|---|---|---|---|---|---|---|---|
| | Compound | | | | | | |
| | (7) | | (27) | | (32) | | |
| | fasted | fed | fasted | fed | fasted | fed | fed |
| 0 | 6.7 | 10.3 | 6.8 | 10.6 | 6.5 | 10.4 | 9.5 |
| 5 | 6.3 | 9.7 | 6.5 | 10.7 | 6.3 | 10.4 | 9.5 |
| 10 | 5.9 | 8.8 | 6.3 | 9.7 | 5.7 | 8.9 | 9.3 |
| 20 | 5.1 | 7.1 | 6.0 | 7.6 | 5.1 | 7.6 | 8.8 |
| 30 | 4.9 | 6.3 | 5.5 | 7.3 | 4.7 | 7.7 | 8.9 |
| 45 | 5.2 | 7.0 | 5.5 | 8.3 | 4.5 | 8.2 | 9.7 |

Thus, the compounds were significantly more effective during hyperglycaemia than during euglycaemia (Max. Δ-glucoe: (7): 4.0 vs. 1.8 mmol/l; (27): 3.3 vs. 1.3 mmol/l; (32): 2.8 vs. 2.0 mmol/l). All values were well above the limits for hypoglycaeumia (>3 mmol/l).

TABLE 2

| Compound Min. after adm. | Insulin levels (pmol/l) after i.v. administration of 10 mg/kg bodyweight to normal rats (fasted or fed) | | | | | | Control fed |
|---|---|---|---|---|---|---|---|
| | Plasma insulin | | | | | | |
| | (7) | | (27) | | (32) | | |
| | fasted | fed | fasted | fed | fasted | fed | fed |
| 0 | 133 | 165 | 137 | 320 | 100 | 120 | 234 |
| 5 | 204 | 623 | 255 | 493 | 262 | 345 | 284 |
| 10 | 177 | 327 | 287 | 403 | 192 | 489 | 223 |
| 20 | 202 | 396 | 282 | 233 | 154 | 265 | 195 |
| 30 | 165 | 297 | 212 | 168 | 106 | 143 | 218 |
| 45 | 122 | 172 | 140 | 115 | 85 | 109 | 300 |

It can be noticed that the compounds caused a much more pronounced increase in insulin secretion in fed rats than in fasted rats.

The activity of the compounds is probably related to their insulin releasing properties (table 2).

Pharmaceutical Compositions

For use in the treatment of type 2 diabetes the compounds of the present invention will generally be available in the form of pharmaceutical compositions. Such compositions may be in the form of powders, solutions, or suspensions, which may or may not be divided in single dose units, or in the form of capsules or tablets.

The pharmaceutical compositions may comprise carriers, diluents, absorption enhancers and other ingredients which are conventionally used in the art.

The route of administration may be any route which effectively transports the active compound to its site of action, the oral or nasal route being preferred.

The daily dose to be administered in therapy will be determined by a physician and will depend on the specific compound employed and on the age and the condition of the patient.

EXAMPLES

The carboxylic acids required as starting materials in the synthesis of the imidazoline derivatives are known from the chemical literature e.g. from British patent applications Nos. 23,888/69, 42,763/69, and 57,434/69 (all to NOVO TERAPEUTISK LABORATORIUM A/S). 5-chlorobenzofuran is described in Indian Academy of Sciences, 338 (1963).

The following examples illustrate the present invention more specifically; however, it should be understood that these examples are given to explain the invention and not to limit the scope of the invention.

EXAMPLE 1

Preparation of 2-[2-[7-(2,3-dihydrobenzofuranyl)]-2-(2-pyridyl)ethyl]-2-imidazoline, (7), using preparation method A 2,3-dihydro-7-benzofuran carbonyl amide (2)

A mixture of $SOCl_2$ (8 ml, 109.64 mmol) in dry THF (10 ml) was added dropwise to a stirred solution of 2,3-dihydro-7-benzofuranylcarboxylic acid (1) (12 g, 73.10 mmol) in dry THF (150 ml) under $N_2$. The reaction mixture was heated to 60° C. for 2 h. After cooling the reaction mixture was added dropwise to an ice cooled vigorously stirred ammonium hydroxide solution (500 ml 25% $NH_3$) maintaining the temperature below 5° C. The reaction mixture was stirred at room temperature for 1 h., concentrated in vacuo, and the residue was extracted with $CH_2Cl_2$ (3×100 ml). The extracts were washed with water (2×60 ml), brine (50 ml), dried ($Na_2SO_4$) and evaporated to yield a solid which was recrystallized from toluene (300 ml) to give (2) as a white solid (10.17 g, 85%).

Mp. 187°-187.8° C.

1H-NMR (80 MHz, $CDCl_3$) δ 7.87 (d, 1H, J=7.47 Hz), 7.35 (bs, 1H, CON$\underline{H}_2$), 7.29 (d, 1H, J=6.93 Hz), 6.9 (t, 1H), 6.07 (bs, 1H, CON$\underline{H}_2$), 4.68 (t, 2H), 3.23 (t, 2H).

| $C_9H_9NO_2$ | % C | % H | % N |
|---|---|---|---|
| Calculated | 66.24 | 5.57 | 8.59 |
| Found | 66.67 | 5.70 | 8.46 |

7-cyano-2,3-dihydro-benzofuran (3)

To a suspension of (2) (10 g, 61.28 mmol) i dry toluene (50 ml) was added $SOCl_2$ (12 ml, 164.92 mmol) under $N_2$. The reaction mixture was heated to 70° C. for 1 h. and then to 90° C. until TLC (AcOEt/Heptane 1:1) indicated complete reaction Water (20 ml) was slowly added to the ice cooled reaction mixture followed by 50% KOH until pH≈8. The organic layer was separated, and the aqueous layer was extracted with toluene (3×50 ml). The combined organic layers were washed with water (2×30 ml), brine (1×30 ml), dried ($Na_2SO_4$), and evaporated in vacuo to yield (3) as a solid (8.81 g, 99%). Recrystallization from abs. EtOH gave (3) as a white solid.

Mp. 54.5°-56° C.

1H-NMR (80 MHz, $CDCl_3$) δ 7.3 (dd, 2H, $H_4+H_6$), 6.82 (t, 1H, $H_5$), 4.7 (t, 2H), 3.24 (t, 2H).

| $C_9H_7NO$ | % C | % H | % N |
|---|---|---|---|
| Calculated | 74.46 | 4.87 | 9.65 |
| Found | 74.66 | 4.87 | 9.55 |

2-pyridyl-[7-(2,3-dihydrobenzofuranyl)]ketone (4)

Dry ether (70 ml) was placed under a $N_2$ atmosphere in a flame dried flask. The flask was cooled to −65° C., and a solution of BuLi in hexane (20.28 ml, 72.74 mmol) was added. To the resulting solution was slowly added a solution of 2-Bromopyridine (7.15 ml, 72.74 mmol) in dry ether (20 ml) maintaining the temperature at −55° C. The colour changed to deep red. The solution was stirred for 15 min. and the a dry ether (50 ml) solution of (3) (8.8 g, 60.62 mmol) was slowly added maintaining the temperature at −50° C. The reaction mixture was heated to −40° C. an stirred for 1 h. and then 1 h. at room temperature. The reaction mixture was poured into 5N HCl (150 ml) and heated to reflux for 2 h. The organic layer was separated, and the aqueous layer was washed (extracted) with ether (3×40 ml) made alkaline with 5N NaOH to pH≈8.5 and extracted with $CH_2Cl_2$ (3×70 ml). The $CH_2Cl_2$ extracts were washed with water (2×40 ml), brine (1×40 ml), dried ($MgSO_4$) and evaporated in vacuo to yield 12.47 g of a brown solid. Recrystallization from abs. EtOH (80 ml) and ether (80 ml) gave 6.43 g of (4). Evaporation and recrystallization of the mother liquid gave an other 918 mg a total of 7.35 g 54% (4) was collected.

Mp. 127.5°-128.5° C.

1H-NMR (400 MHz, $CDCl_3$) δ 8.69 (d, 1H), 7.90 (d, 1H), 7.88 (t, 1H), 7.57 (d, 1H), 7.54 (dd, 1H), 6.95 (t, 1H), 4.60 (t, 2H), 3.24 (t, 2H).

| $C_{14}H_{11}NO_2$ | % C | % H | % N |
|---|---|---|---|
| Calculated | 74.64 | 4.93 | 6.22 |
| Found | 74.96 | 4.89 | 6.17 |

Ethyl 3-[7-(2,3-dihydrobenzofuranyl)]-3-(2-pyridyl)acrylate (5)

Sodium (920 mg, 40 mmol) was dissolved in dry EtOH (20 ml). The solution was cooled to −10° C. and a solution of triethyl phosphonoacetate (8.97 g, 40 mmol) in dry EtOH (5 ml) was added maintaining the temperature at −5° C. The reaction mixture was allowed to reach 10° C. and stirred for 15 min. (4) (6.40 g , 30 mmol) was added at −5° C. and the resulting mixture heated to 60° C. for 3 h. The bulk of the EtOH was evaporated, and the resulting mass was dissolved in $CH_2Cl_2$ (100 ml) and washed with water (3×30 ml), brine (1×20 ml), dried $MgSO_4$ and evaporated in vacuo to yield 8.86 g (100%) of (5) as a oil.

The Z- and E-isomers could be separated using chromatography (AcOEt/Heptane 1:1).

1. isomer Mp. 124.3°-125.2° C.

1H-NMR (80 MHz, $CDCl_3$) of the 1.-isomer δ 8.58 (d, 1H), 7.63 (t, 1H), 7.17 (m, 2H), 6.90 (s, 1H), 6.62 (m, 2H, incl. the methine), 4.55 (t, 2H), 3.97 (q, 2H), 3.14 (t, 2H), (1.04 (t, 3H).

2. isomer Mp. 73.5°-75° C.

1H-NMR (80 MHz, $CDCl_3$) of the 2.-isomer δ 8.60 (d, 1H), 7.53 (t, 1H), 7.22-6.82 (m, 5H, incl. the methine), 4.45 (t, 2H), 4.05 (q, 2H), 3.19 (t, 2H), 1.12 (t, 3H).

Ethyl 3-[7-(2,3-dihydrobenzofuranyl)]-3-(2-pyridyl)propionate (6)

(5) (4.6 g, 15.57 mmol) in dry EtOH (200 ml) was hydrogenated over 10% Pd/C (2 g) catalyst in room temperature under atmospheric pressure. When $H_2$ absorption ceased the catalyst was filtered off and the filtrate was concentrated in vacuo to give 4.08 g (88%) of (6) as a colourless oil.

1H-NMR (80 MHz, $CDCl_3$) δ 8.48 (d, 1H), 7.50 (t, 1H), 7.13-6.63 (m, 5H), 4.83 (dd, 1H, C$\underline{H}$—$CH_2$), 4.50

(t, 2H), 4.00 (q, 2H), 3.42 (dd, 1H, CH—CH$_2$), 3.13 (t, 2H), 2.95 (dd, 1H, CH—CH$_2$), 1.07 (t, 3H).

2-[2-[7-(2,3-dihydrobenzofuranyl)]-2-(2-pyridyl)ethyl]-2-imidazoline (7)

Trimethylaluminum (12.35 ml, 24.70 mmol, 2.0 M in toluene) was placed under a N$_2$ atmosphere in a flame dried flask. Ethylenediamine (1.66 ml, 24.70 mmol) was added at −10° C. and the mixture was stirred at room temperature until the methane evolution ceased. A solution of (6) (4.59 g, 15.44 mmol) in dry toluene was added and the resulting mixture was heated to reflux for 4 h. The reaction was quenched at 0° C. with a mixture of water (25 ml), MeOH (90 ml) and CH$_2$Cl$_2$ (90 ml). The resulting mixture was refluxed for 15 min., filtered through Na$_2$SO$_4$ (3 cm) and evaporated in vacuo, yielding a foam 5.5 g. The foam was dissolved in AcOEt (60 ml) and refluxed for 30 min. to remove traces of aluminum hydroxide from the crude product. Filtration of the hot solution over Na$_2$SO$_4$ (2 cm) and removal of the solvent in vacuo, gave crude (7) (4 g, 88%). Analytically pure samples were obtained by kugelrohr distillation and recrystallization from acetone.

Mp. 144.5°–145.7° C.

$^1$H-NMR (400 MHz, CDCl$_3$) δ 8.54 (d, 1H), 7.54 (t, 1H), 7.25 (d, 1H), 7.10 (t, 1H), 7.02 (dd, 2H), 6.76 (t, 1H), 4.73 (dd, 1H, CH—CH$_2$), 4.55 (t, 2H), 3.60 (bs, 4H, CH$_2$—CH$_2$), 3.31 (dd, 1H, CH—CH$_2$), 3.19 (t, 2H), 2.96 (dd, 1H, CH—CH$_2$).

| C$_{18}$H$_{19}$N$_3$O | % C | % H | % N |
|---|---|---|---|
| Calculated | 73.68 | 6.54 | 14.33 |
| Found | 73.67 | 6.67 | 14.00 |

EXAMPLE 2

Preparation of
2-[2-[7-(2,3-dihydrobenzofuranyl)]-2-(4-fluorophenyl)ethyl]-2-imidazoline, (11), using preparation method A 4-fluorophenyl-[7-(2,3-dihydrobenzofuranyl)]ketone (8)

To a solution of 2,3-dihydro-7-cyanobenzofuran, (3) (3 g, 20.67 mmol) in dry THF (80 ml) was added a solution of 4-fluorophenylmagnesium bromide (≈41.33 mmol) in dry THF (25 ml). The resulting mixture was refluxed for 4.5 h. cooled to −5° C., 5N HCl (150 ml) was added and the mixture extracted with CH$_2$Cl$_2$ (2×80 ml). To the resulting water phase was added toluene (80 ml) and the mixture heated to reflux for 4 h. The layer was separated and the water layer was extracted with toluene (3×50 ml). The combined organic layers were washed with water (30 ml), brine (30 ml), dried MgSO$_4$ and evaporated in vacuo, yielding (8) (3.84 g, 77%) as green crystals. Recrystallization from EtOH (30 ml) gave (8) as white crystals.

Mp. 120.5°–121.7° C.

$^1$H-NMR (80 MHz, CDCl$_3$) δ 7.83 (m, 2H), 7.37 (m, 5H), 4.55 (t, 2H), 3.19 (t, 2H).

Ethyl 3-[7-(2,3-dihydrobenzofuranyl).-3-(4-fluorophenyl)acrylate (9)

Sodium (560 mg, 24.35 mmol) was dissolved in dry EtOH (20 ml). The solution was cooled to −10° C. and a solution of triethylphosphonoacetate (4.45 ml, 22.41 mmol) in dry EtOH (6 ml) was added maintaining the temperature at −5° C. The reaction mixture was allowed to reach 10° C. and stirred for 15 min. (8) was added at −5° C. and the resulting mixture heated to 60° C. for 18 h. The bulk of the EtOH was evaporated, and the resulting mass was dissolved in CH$_2$Cl$_2$ (100 ml) and washed with water (3×30 ml), brine (1×20 ml), dried MgSO$_4$ and evaporated in vacuo to yield 5.99 g of (9) as a bright tea coloured oil, which was used without further purification.

$^1$H-NMR (80 MHz, CDCl$_3$) δ 7.40–6.63 (m, 7H), (6.83 for E and 6.30 for Z (2 s, 1H), 4.53 (m, 2H), 4.05 (m, 2H), 3.20 (t, 2H), 1.18 (m, 3H).

Ethyl 3-7-(2,3-dihydrobenzofuranyl)]-3-(4-fluorophenyl)propionate (10)

(10) Was prepared in a way similar to the one described for (6). The crude product was purified by chromatography (toluene) yielding (10) (88% from (8) ) as a oil.

$^1$H-NMR (80 MHz, CDCl$_3$) δ 7.25 (m, 2H), 6.87 (m, 5H), 4.57 (m, H), 3.97 (q, 2H), 3.09 (m, 4H), 1.07 (t, 3H).

2-[2-7-(2,3-dihydrobenzofuranyl)]-2-(4-fluorophenyl)1-ethyl-2-imidazoline (11)

(11) was prepared in a way similar to the one described for (7).

Mp. 107.5°–108.5° C.

$^1$H-NMR (80 MHz, CDCl$_3$) 7.22 (m, 2H), 6.88 (m, 5H), 4.48 (t, 2H, O—CH$_2$—CH$_2$), 3.65 (bs, 1H, NH), 3.38 (s, 4H, CH$_2$—CH$_2$), 3.03 (t, 2H, O—CH$_2$—CH$_2$).

| C$_{19}$H$_{19}$N$_2$FO.$\frac{1}{4}$ H$_2$O | % C | % H | % N |
|---|---|---|---|
| Calculated | 71.44 | 6.32 | 8.77 |
| Found | 71.48 | 6.33 | 8.38 |

EXAMPLE 3

Preparation of
2-[2-[7-(2,3,5-trimethyl-benzofuranyl)]-2-(2-pyridyl)ethyl]-2-imidazoline, (17), using preparation method A 2,3,5-trimethyl-2,3-dihydro-7-benzofuran carbonyl amide (12)

(12) was prepared in a way similar to the one described for (2).

Mp. 158.5°–160.5° C.

$^1$H-NMR (80 MHz, CDCl$_3$) δ 7.70 (s, 1H), 7.47 (bs, 1H, CONH$_2$), 7.02 (s, 1H), 6.00 (bs, 1H, CONH$_2$), 5.00 (m) and 4.47 (m) (1H, pair of diastereomers), 3.40 (m) and 3.07 (m) (1H, pair of diastereomers), 2.30 (s, 3H), 1.53–1.13 (4 dd, 6H, could not be assigned)

7-cyano 2,3,5-trimethyl-2,3-dihydro-benzofuran (13)

(13) was prepared in a way similar to the one described for (3).

$^1$H-NMR (80 MHz, CDCl$_3$) δ 7.02 (bs, 2H), 4.97 (m) and 4.45 (m) (1H, pair of diastereomers), 3.40 (m) and 3.10 (m) (1H, pair of diastereomers), 2.21 (s, 3H), 1.48–1.07 (4 dd, 6H).

2-pyridyl-[7-(2,3,5-trimethyl-2,3-dihydrobenzofuranyl)]ketone (14)

(14) was prepared in a way similar to the one described for (4). (14) was purified by kugel rohr distillation (220° C., 0.2 mmHg) yielding (14) as a oil.

$^1$H-NMR (80 MHz, CDCl$_3$) δ 8.63 (d, 1H), 8.03 - 7.07 (m, 5H), 4.82 (m) and 4.30 (m) (1H, pair of diastereomers), 3.33 (m) and 2.95 (m) (1H, pair of diastereomers), 2.26 (s, 3H), 1.37–1.12 (4 dd, 6H, could not be assigned).

Ethyl 3-[7-(2,3,5-trimethyl-2,3-dihydrobenzofuranyl)]-3-(2-pyridyl)acrylate (15)

(15) was prepared in a way similar to the one described for (9). (15) was isolated as a coloured oil, which was used without further purification.

$^1$H-NMR (80 MHz, CDCl$_3$) δ 8.60 (d, 1H), 7.77–6.83 (m, 5H), 6.60 and 6.40 (2 s, 1H, C=CH), 4.83 (m) and 4.12 (m) (3H, O—CH(CH$_3$) and COO—CH$_2$—CH$_3$), 3.22 (m) and 2.95 (m) (1H, CH(CH$_3$)), 2.27 (s) and 2.12 (s) (3H, aromate-CH$_3$), 1.43–0.97 (m, 9H, O—CH(CH$_3$)—CH(CH$_3$), COO—CH$_2$—CH$_3$).

Ethyl 3-[7-(2,3,5-trimethyl-2,3-dihydrobenzofuranyl)]-3-(2-pyridyl)propionate (16)

(16) was prepared in a way similar to the one described for (6). (16) was purified by chromatography (AcOEt/Heptane 1:3) yielding (16) as an oil.

$^1$H-NMR (80 MHz, CDCl$_3$) δ 8.48 (d, 1H), 7.57–6.73 (m, 5H), 4.82 (m) and 4.23 (m) (2H, CH—CH$_2$, O—CH—(CH$_3$)), 4.02 (q, 2H), 3.42 (m) and 2.95 (m) (3H, CH—CH$_2$, O—CH(CH$_3$)—CH(CH$_3$)), 4.00 (q, 2H, CH—CH$_2$), 2.17 (s, 3H), 1.42–0.98 (m, 9H, O—CH(CH$_3$)—CH(CH$_3$), COOCH$_2$—CH$_3$)

2-[2-[7-(2,3,5-trimethyl-2,3-dihydrobenzofuranyl)]-2-(2-pyridyl)ethyl]-2-imidazoline (17)

(17) was prepared in a way similar to the one described for (7) The crude product was purified by chromatography (Al$_2$O$_3$, 5% EtOH in CH$_2$Cl$_2$). The product contains all six isomers. TLC (Al$_2$O$_3$, 5% EtOH in CH$_2$Cl$_2$): one spot.

Mp. 110°–114° C.

$^1$H-NMR (400 MHz, d$_6$-acetone) δ 8.48 (d, 1H), 7.56 (t, 1H), 7.23 (dd, 1H), 7.10 (t, 1H), 6.84 (bs, 1H), 6.77 (d, 1H), 4.81 (m, 1,5H, CH—CH$_2$, O—CH(CH$_3$)—CH), 4.28 (sextet, 0.5H, O—H(CH$_3$)—CH), 3.31 (m, 5.5H, CH$_2$—CH$_2$, CH—CH$_2$, O—CH(CH$_3$)—CH(CH$_3$)), 2.98 (sextet, 0.5H, O—CH(CH$_3$)—CH(CH)$_3$), 2.77 (dd, 1H, CH—CH$_2$), 2.16 (s, 3H, CH$_3$), 1,27 (m, 3H, O—CH(CH$_3$)), 1.12 (m, 3H, O—CH(CH$_3$)—CH(CH$_3$)).

| C$_{21}$H$_{25}$N$_3$O.½ H$_2$O | % C | % H | % N |
|---|---|---|---|
| Calculated | 73.21 | 7.62 | 12.20 |
| Found | 73.53 | 7.71 | 12.08 |

EXAMPLE 4

Preparation of 2-[2-[7-(2,2,5-trimethyl-2,3-dihydrobenzofuranyl)]-2-(2-pyridyl)ethyl]-2-imidazoline (23), using preparation method A

2,2,5-trimethyl-2,3-dihydro-7-benzofuran carbonyl amide (18)

(18) was prepared in a way similar to the one described for (2).

Recrystallized from heptane.

Mp. 129°–130° C.

$^1$H-NMR (400 MHz, CDCl$_3$) δ 7.68 (s, 1H), 7.53 (bs, 1H), 7.06 (s, 1H), 5.97 (bs, 1H), 3.02 (s, 2H), 2.30 (s, 3H), 1.52 (s, 3H).

7-cyano-2.2.5.trimethyl-2,3-dihydrobenzofuran (19)

(19) was prepared in a way similar to the one described for (3).

$^1$H-NMR (400 MHz, CDCl$_3$) δ 7.11 (s, 1H), 7.06 (s, 1H) 2.99 (s, 2H), 2.25 (s, 3H), 1.52 (s, 6H)

2-pyridyl-[7-(2,2,5-trimethyl-2,3-dihydrobenzofuranyl)]-hetone (20)

(20) was prepared in a way similar to the one described for (4). (20) was purified by chromatography (AcOEt/cyclohexane 1:2).

$^1$H-NMR (400 MHz, CDCl$_3$) δ 8.63 (d, 1H), 7.89 (d, 1H), 7.81 (t, 1H), 7.41 (dd, 1H), 7.33 (s, 1H), 7.11 (s, 1H), 2.94 (s, 2H), 2.30 (s, 3H), 1.36 (s, 6H).

Ethyl 3-[7-(2,2,5-trimethyl-2,3-dihydrobenzofuranyl)]-3-(2-pyridyl)acrylate (21)

(21) was prepared in a way similar to the one described for (5).

$^1$H-NMR (400 MHz, CDCl$_3$) δ 8.63 (t, 1H), 7.67 and 7.56 (two t, 1H), 7.28–7.09 (m, 3H), 6.96 and 6.89 (two s, 2H), 6.71 and 6.42 (two s, 1H), 4.07 and 4.00 (two q, 2H), 2.99 and 2.94 (two s, 2H), 2.26 and 2.12 (two s, 3H), 1.42 and 1.35 (two s, 6H), 1.15 and 1.09 (two t, 3H).

Ethyl 3-[7-(2,2,5-trimethyl-2,3-dihydrobenzofuranyl)]-3-(2-pyridyl)propionate (22)

(22) was prepared in a way similar to the one described for (6).

$^1$H-NMR (400 MHz, CDCl$_3$) 8.50 (d, 1H), 7.50 (t, 1H), 7.23 (d, 1H), 7.04 (t, 1H), 6.76 (ds, 2H), 4.79 (dd, 1H, CH—CH$_2$), 4.05 (q, 2H), 3.44 (dd, 1H, CH—CH$_2$), 2.98 (dd, 1H, CH—CH$_2$), 2.93 (s, 2H), 2.19 (s, 3H), 1.41 (s, 6H), 1,13 (t, 3H).

2-[2-[7-(2,2,5-trimethyl 2,3-dihydrobenzofuranyl)]-2-(2pyridyl) ethyl]-2-imidazoline (23)

(23) was prepared in a way similar to the one described for (7).

Mp. 80.3°–81.4° C.

$^1$H-NMR (400 MHz, CDCl$_3$) 8.51 (d, 1H), 7.52 (dt, 1H), 7.26 (d, 1H), 7.07 (t, 1H), 6.79 (ds, 2H), 4.66 (dd, 1H, CH—CH$_2$), 3.42 (bs, 4H, CH$_2$—CH$_2$), 3.32 (dd, 1H, CH—CH$_2$), 2.95 (dd, 1H, CH—CH$_2$), 2.93 (s, 2H), 2.19 (s, 3H).

EXAMPLE 5

Preparation of 2-[2-[7-(2,3-dihydrobenzofuranyl)]-2-(2-pyridyl)ethyl]-2-imidazoline, (7), using preparation method B

2-pyridyl-[7-(2 3-dihydrobenzofuranyl)]ketone (4)

2,3-dihydrobenzofuran (12.01 g, 100 mmol) was mixed with dry Bu$_2$O (200 ml). A mixture of BuLi (40 ml of a 2.5 M solution in hexane, 100 mmol) and dry Bu$_2$O (50 ml) was added dropwise with stirring at 5°–10° C., When the addition was completed the temperature of the mixture was allowed to reach room temperature and the mixture was then immersed in an oil bath at 90° C. for 16 hours. The mixture was then cooled to 5° C. and a solution of 2-cyano-pyridine (10.41 g, 100 mmol) in dry Bu$_2$O (50 ml) was added dropwise. After stirring at room temperature for 60 hours the reaction mixture was hydrolysed with ice cold HCl, made alkaline with NaOH and extracted with Et₂O. The ether extract was dried over Na₂SO₄ and the ether was evaporated. The residue was chromatographed on silica gel and the product was recrystallised from EtOH. Yield: 15 g (70%) of the desired intermediate. Mp. 125°–6° C.

| C₁₄H₁₁NO₂ | % C | % H | % N |
| --- | --- | --- | --- |
| Calculated | 74.65 | 4.92 | 6.22 |
| Found | 74.80 | 4.93 | 6.21 |

Ethyl 3-[7-(2.3-dihydrobenzofuranyl)]-3-(2-pyridyl)-acrylate

Sodium (0.92 g, 40 mmol) was dissolved in dry EtOH (30 ml). At 5°–10° C. triethyl phosphonoacetate (8.97 g, 40 mmol) was added to the sodium ethanolate solution and the mixture was stirred at 5° C. for 10 minutes. (4) (30 mmol) was added to the cold solution of the Wittig reagent and the mixture was allowed to reach room temperature. After stirring for 20 hours the solvent was removed in vacuo. The residue was triturated with water, the pH being adjusted to 7 with 4 N HCl, and this mixture was extracted once with Et₂O. The ether phase was discarded. The water phase was made alkaline with 4 N aqueous NaOH and extracted with CH₂Cl₂. The extract was shaken with saturated aqueous NaCl and dried over Na₂SO₄. The solvent was removed in vacuo to leave 8.86 g (100%) of crude product. TLC on silica gel (AcOEt/CH₂Cl₂ 1:9) revealed two spots which were supposed to be the Z and E isomer respectively of the desired compound.

Ethyl 3-[7-(2,3-dihydrobenzofuranyl)]-3-(2-pyridyl)-propionate (6)

(5) (5.9 g, 20 mmol, crude product) was dissolved in warm EtOH (70 ml, 99%). The mixture was diluted with more EtOH (70 ml, 99%) and cooled to room temperature. 10% palladium on carbon (300 mg) was added and the mixture was hydrogenated at atmospheric pressure. The consumption of hydrogen was 450 ml. The catalyst was filtered off and the filtrate evaporated to leave 5.65 g (95%) of crude product. After purification on silica gel a yield of 4,76 g (80%) of the desired product was obtained.

2-[2-[7-(2,3-dihydrobenzofuranyl)]-2-(2-pyridyl)ethyl]-2-imidazoline (7)

(6) (2.97 g, 10 mmol, crude product) was mixed with ethylenediamine (6.01 g, 100 mmol (dried, redistilled)) and the mixture was refluxed under N₂ for 24 hours. Water, EtOH and excess ethylenediamine was then distilled off at atmospheric pressure under N₂. During the final stage of the distillation the temperature of the heating bath was raised to 250° C. Still under N₂ the distillation flask was allowed to cool to room temperature. Magnesium powder (0.24 g, 10 mmol) was added, and the heating of the flask was resumed, this time in a bath at 240° C., still under N₂. After 2 hours the contents of the flask were distilled at 0.1 mmHg. The flask was heated to about 300° C. and distillate was collected over the boiling point range 206°–216° C. The distillate crystallised on cooling and was recrystallised from acetone. Yield: 0.44 g of the title compound, (7). Mp. 145.5°–146° C.

| C₁₈H₁₉N₃O | % C | % H | % N |
| --- | --- | --- | --- |
| Calculated | 73.69 | 6.53 | 14.32 |
| Found | 73.65 | 6.54 | 14.07 |

Analytical data in agreement with corresponding data from example 1.

EXAMPLE 6

Preparation of 2-[2-[5-(2,3-dihydrobenzofuranyl)]-2-(2-pyridyl)ethyl]-2-imidazoline, (27), using a first version (cf. Example 7) of preparation method C 2-pyridyl-[5-(2,3-dihydrobenzofuranyl]ketone (24)

2,3-dihydrobenzofuran-5-magnesiumbromide (85.61 g, 0.36 M) in dry THF was added dropwise to a cooled solution (ice bath) of 2-cyano pyridine (28.21 g, 0.28 M) in dry THF (300 ml). The mixture was allowed to reach room temperature and stirred for 24 h. Then hydrolysed (5 N HCl), basified (5 N NaOH), extracted with AcOEt (3×150 ml), dried (Na₂SO₄) and evaporated to yield crude (24) which was purified by chromatography (10% AcOEt/Toluene) and recrystallized from Et₂O. Yield 28.62 g 35%.

Mp. 67°–68° C.

¹H-NMR (400 MHz, CDCl₃) δ 8.67 (d, 1H), 7.94 (t, 3H), 7.86 (dt, 1H), 7.42 (m, 1H), 6.81 (d, 1H), 4.66 (t, 2H), 3.26 (t, 2H).

| C₁₄H₁₁NO₂ | % C | % H | % N |
| --- | --- | --- | --- |
| Calculated | 74.65 | 4.92 | 6.22 |
| Found | 74.93 | 4.98 | 6.08 |

3-[5-(2,3-dihydrobenzofuranyl)]-3-(2-pyridyl)acrylonitrile (25)

Sodium (1.26 mg, 55 mmol) was dissolved in dry EtOH (50 ml). The solution was cooled to −10° C. and a solution of diethyl cyanomethylphosphonate (9.41 g, 55 mmol) was added dropwise maintaining the temperature at −5° C. The reaction mixture was allowed to reach 10° C. and stirred for 15 min. (24) (11.26 g, 50 mmol) was added at −5° C. and the resulting mixture heated to reflux for 16 h. The bulk of the EtOH was evaporated, and the resulting mass was dissolved in CH₂Cl₂(150 ml) and washed with water (3×50 ml), brine (1×50 ml), dried Na₂SO₄ and evaporated in vacuo to yield crude (25).

(25) was purified using chromatography (AcOEt/Heptane 1:1) yield 8.69 g.

Mp. 74°–75° C.

¹H-NMR (400 MHz, CDCl₃) δ 8.68 (d, 1H), 7.67 (dt, 1H), 7.34 (t, 2H), 7.21 (t, 2H), 6.88 (d, 1H), 6.47 (s, 1H, methine), 4.66 (t, 2H), 3.28 (t, 2H).

3-[5-(2,3-dihydrobenzofuranyl)]-3-(2-pyridyl)propionitrile (26)

(26) was prepared in a way similar to the one described for (6).

¹H-NMR (400 MHz, CDCl₃) δ 8.60 (d, 1H), 7.60 (dt, 1H), 7.15 (m, 3H), 7.03 (dd, 1H), 6.72 (d, 1H), 4.54 (t, 2H), 4.37 (t, 1H, C$\underline{H}$—CH₂), 3.34 (dd, 1H, CH—C$\underline{H}$₂), 3.16 (t, 2H), 3.05 (d$\underline{d}$, 1H, CH—C$\underline{H}$₂).

2-[2-[5-(2,3-dihydrobenzofuranyl)]-2-(2-pyridyl)ethyl]-2-imidazoline (27)

(26) (0.98 g, 3.90 mmol), was mixed with ethylene diamine (4 ml) and phosphorous pentasulfide (150 mg). The mixture was heated to 80° C. for 20 h. To the cooled mixture was added EtOH/H$_2$O 1:1 (50 ml) and the mixture was stirred for 30 min. The mixture was extracted with CH$_2$Cl$_2$ (3×20 ml), dried (Na$_2$SO$_4$) and evaporated in vacuo to yield crude (27) which was purified by chromatography (basic Al$_2$O$_3$, 20% EtOH/CH$_2$Cl$_2$). Yield 366 mg 32%.
Mp. 127°-128° C.

$^1$H-NMR (400 MHz, CDCl$_3$) δ 8.54 (d, 1H), 7.54 (t, 1H), 7.14 (d, 2H), 7.11 (t, 1H), 7.04 (d, 1H), 6.66 (d, 1H), 4.53 (t, 2H), 4.46 (t, 1H), 3.42 (bs, 4H), 3.27 (dd, 1H), 3.15 (t, 2H), 2.88 (dd, 1H).

| C$_{18}$H$_{19}$N$_3$O | % C | % H | % N |
|---|---|---|---|
| Calculated | 73.68 | 6.54 | 14.33 |
| Found | 73.32 | 6.69 | 13.91 |

EXAMPLE 7

Preparation of 2-[2-[5-(2,3-dihydrobenzofuranyl)]-2-(2-pyridyl)ethyl]-2-imidazoline, (27), using a second version (c.f. Example 6) of preparation method C Ethyl 3-[5-(2,3-dihydrobenzofuranyl)-3-(2-pyridyl)-acrylate (28)

(28) was prepared in a way similar to the one described for (5). The crude product was used without further purification.

Ethyl 3-[5-(2,3-dihydrobenzofuranyl)-3-(2-pyridyl)-propionate (29)

(29) was prepared in a way similar to the one described for (6).

$^1$H-NMR (400 MHz, CDCl$_3$) δ 8.58 (d, 1H), 7.58 (t, 1H), 7.18 (d, 2H), 7.11 (dd, 1H), 7.07 (d, 1H), 6.70 (d, 1H), 4.54 (m, 3H), 4.06 (q, 2H), 3.40 (dd, 1H), 3.16 (t, 2H), 2.26 (dd, 1H), 1.14 (t, 3H).

2-[2-[5-(2,3-dihydrobenzofuranyl)]-2-(2-pyridyl)ethyl]-2-imidazoline (27)

(27) was prepared in a way similar to the one described for (7). (27) was purified by chromatography (Al$_2$O$_3$, 10% EtOH in AcOEt).
Mp. 127.5°-128.4° C.

$^1$H-NMR (400 MHz, CDCl$_3$) δ 8.53 (d, 1H), 7.56 (dt, 1H), 7.15 (d, 2H), 7.11 (t, 1H), 7.05 (d, 1H), 6.67 (d, 1H), 4.50 (t, 2H), 4.44 (t, 1H, C$\underline{H}$—CH$_2$), 3.43 (bs, 4H, CH$_2$—C$\underline{H}_2$), 3.27 (dd, 1H, CH—C$\underline{H}_2$), 3.14 (t, 2H), 2.88 (dd, 1H, CH—C$\underline{H}_2$).

| C$_{18}$H$_{19}$N$_3$O | % C | % H | % N |
|---|---|---|---|
| Calculated | 73.68 | 6.54 | 14.33 |
| Found | 73.50 | 6.67 | 14.02 |

EXAMPLE 8

Preparation of 2-[2-(2-benzofuranyl)-2-(2-pyridyl)ethyl]-2-imidazoline, (32), using preparation method D Ethyl 3-(2-benzofuranyl)-3-(2-pyridyl)acrylate (30)

(30) was prepared in a way similar to the one described for (5). The crude product was distilled and the fraction boiling at 198° C./0.05 mmHg was collected. The product was recrystallized from Et$_2$O. Yield 88%
Mp. 88°-89° C.

$^1$H-NMR (400 MHz, CDCl$_3$) δ 8.67 (d, 1H), 7.68 (dt, 1H), 7.59 (d, 1H), 7.45 (d, 1H), 7.33 (m, 3H), 7.25 (d, 1H), 7.02 (s, 1H), 6.90 (s, 1H), 4.21 (q, 2H), 1.20 (t, 3H).

| C$_{18}$H$_{15}$NO$_3$ | % C | % H | % N |
|---|---|---|---|
| Calculated | 73.70 | 5.16 | 4.78 |
| Found | 73.89 | 5.20 | 4.63 |

Ethyl 3-(2-benzofuranyl)-3-(2-pyridyl)propionate (31)

(31) was prepared in a way similar to the one described for (6). The crude product was purified by chromatography (10% AcOEt in CH$_2$Cl$_2$) Yield 90%.

$^1$H-NMR (400 MHz, CDCl$_3$) δ 8.56 (d, 1H), 7.61 (dt, 1H), 7.45 (dd, 1H), 7.38 (dd, 1H), 7.29 (d, 1H], 7.15 (m, 3H), 6.49 (s, 1H), 4.85 (t, 1H), 4.09 (q, 2H), 3.38 (dd, 1H), 3.20 (dd, 1M), 1.17 (t, 3H).

2-[2-(2-benzofuranyl)-2-(2-pyridyl)ethyl-2-imidazoline (32)

(32) was prepared in a way similar to the one described for (7). The crude product was purified by chromathography (basic Al$_2$O$_3$, 20% i-PrOH in AcOEt). Recrystallized from AcOEt. Yield 38%.
Mp. 109°-111.6° C.

$^1$H-NMR (400 MHz, CDCl$_3$) δ 8.56 (d, 1H), 7.62 (dt, 1H), 7.48 (d, 1H), 7.39 (d, 1H), 7.27 (d, 1H), 7.18 (m, 3H), 6.56 (s, 1H), 4.77 (t, 1H), 3.47 (bs, 5H, N$\underline{H}$, C$\underline{H}_2$—C$\underline{H}_2$), 3.25 (dd, 1H), 3.16 (dd, 1H).

| C$_{18}$H$_{17}$N$_3$O.H$_2$O | % C | % H | % N |
|---|---|---|---|
| Calculated | 73.21 | 7.62 | 12.20 |
| Found | 73.53 | 7.71 | 12.08 |

EXAMPLE 9

Preparation of 2-[2-[7-(5-chloro-2,3-dihydrobenzofuranyl)]-2-(2-pyridyl)ethyl]-2-imidazoline, (3s), using preparation method E 5-chloro-2,3-dihydrobenzofuran (33)

5-Chloro-benzofurane (2 g, 13.11 mmol) in dry EtOH (20 ml) was hydrogenated over 10% Rh/C (251 mg) catalyst at room temperature under atmospheric pressure. When H$_2$ absorption ceased the catalyst was filtered off and the filtrate was concentrated in vacuo to give 1.84 g (91%) of (33) as a colourless solid. $^1$H-NMR (80 MHz, CDCl$_3$) δ 7.00 (d, 2H, J=8.53 Hz), 6.62 (d, 1H, J=8.53), 4.5 (t, 2H), 3.11 (t, 2H).

5-chloro-7-bromo-2,3-dihydrobenzofuran (34)

To a stirred solution of (33) (1.84 g, 11.93 mmol) in acetic acid (10 ml) at 0° C., was slowly added a solution of bromine (1.24 ml, 24 mmol) in acetic acid (5 ml). The reaction mixture was stirred at room temperature for 4.5 h. A 10% sodium thiosulphate solution (70 ml) was added and the mixture stirred for 10 min. The bulk of the solvent was evaporated in vacuo. The resulting oil was dissolved in ether (50 ml), washed with water (20 ml), saturated $NaHCO_2$ (2×15 ml), brine (1×15 ml), dried $Na_2SO_4$ and evaporated in vacuo to give 2.55 g (92%) of (34) as a oil.

$^1$H-NMR (80 MHz, $CDCl_3$) δ 7.18 (s, 1H), 7.00 (s, 1H), 4.60 (t, 2H), 3.21 (t, 2H).

2-pyridyl-[7-(5-chloro-2,3-dihydrobenzofuranyl)]ketone (35)

To a solution of 2-cyano-pyridine (3.53 ml, 36.24 mmol) in dry THF (15 ml) at 0° C., was slowly added a solution of 5-chloro-2,3-dihydrobenzofuranyl-7-magnesium bromide (≈32.95 mmol, made from (34) and Mg (921.1 mg) in dry THF) in dry THF (50 ml) maintaining the temperature below 10° C. The resulting mixture was refluxed for 2 h. cooled to −5° C., 5N HCl (100 ml) was added and the mixture refluxed for 2 h. The water/THF phase was extracted with ether (2×80 ml), neutralized with 5N NaOH (≈100 ml) and extracted with $CH_2Cl_2$ (4×80 ml). The combined dried $MgSO_4$ and evaporated in vacuo, yielding (35) (6.04 g, 71%) as green crystals. (35) was purified by chromatography (10% AcOEt in $CH_2Cl_2$) yielding (35) 3.25 g (38%) as a orange solid. Recrystallization from EtOH gave a analytically pure sample.

Mp. 139°–140° C.

$^1$H-NMR (80 MHz, $CDCl_3$) δ 8.63 (d, 1H), 8.03–7.23 (m, 5H), 4.55 (t, 2H), 3.17 (t, 2H).

| $C_{14}H_{10}NClO_2$ | % C | % H | % N | % Cl |
|---|---|---|---|---|
| Calculated | 64.75 | 3.89 | 5.39 | 13.65 |
| Found | 64.68 | 3.94 | 5.32 | 13.69 |

Ethyl 2-pyridyl-[7-(5-chloro-2,3-dihydrobenzofuranyl)]acrylate (36)

(36) was prepared in a way similar to the one described for (9). (36) was isolated as a coloured oil, used without further purification. TLC on silica gel (AcOEt/Heptane 1:1) revealed two spots which were supposed to be the Z and E isomer of (36).

$^1$H-NMR (80 MHz, $CDCl_3$) δ 8.58 (d, 1H), 7.57 (t, 1H), 7.11 (m, 4H), 6.87 and 6.60 Z and E (2 s, 1H, C=C$\underline{H}$), 4.53 (q, 2H), 4.02 (m, 2H), 3.17 (t, 2H), 1.1 (q, 3H).

Ethyl 2-pyridyl-[7-(5-chloro-2,3-dihydrobenzofuranyl)]propionate (37)

(36) (6.84 g, 20.734 mmol) in dry EtOH (150 ml) was hydrogenated over 10% Rh/C (1.5 g) catalyst at room temperature under atmospheric pressure. When $H_2$ absorption ceased the catalyst was filtered off and the filtrate was concentrated in vacuo to give 6.32 g of a oil witch was purified by chromatography (5% AcOEt in $CH_2Cl_2$) yielding (37) 4.89 g (71%) as a oil.

$^1$H-NMR (80 MHz, $CDCl_3$) δ 8.47 (d, 1H), 7.50 (t, 1H), 7.07 (m, 4H), 4.7 (dd, 1H, CH—C$\underline{H_2}$), 4.51 (t, 2H), 4.03 (q, 2H), 3.37 (dd, 1H, CH—C$\underline{H_2}$), 3.10 (t, 2H), 2.91 (dd, 1H, CH—C$\underline{H_2}$), 1.10 (t, 3H).

2-[2-[7-(5-chloro-2,3-dihydrobenzofuranyl)]-2-(2-pyridyl)ethyl]-2-imidazoline (38)

(38) was prepared in a way similar to the one described for (7). (3s) was purified by crystallization (acetone).

Mp. 150.5°–151.7° C.

$^1$H-NMR (400 MHz, $CDCl_3$) δ 8.55 (d, 1H), 7.56 (dt, 1H), 7.22 (d, 1H), 7.12 (t, 1H), 6.98 (s, 1H), 6.96 (s, 1H), 4.69 (dd, 1H, CH—C$\underline{H_2}$), 4.57 (t, 2H), 3.58 (bs, 4H, C$\underline{H_2}$—C$\underline{H_2}$), 3.27 (dd, 1H, CH—C$\underline{H_2}$), 3.17 (t, 2H), 2.89 (dd, 1H, CH—C$\underline{H_2}$).

| $C_{18}H_{18}N_3ClO$ | % C | % H | % N | % Cl |
|---|---|---|---|---|
| Calculated | 65.94 | 5.55 | 12.82 | 10.81 |
| Found | 65.88 | 5.64 | 12.51 | 10.80 |

EXAMPLE 10

Preparation of 2-[2-[7-(5-methoxy-2-methyl-benzofuranyl)]-2-(2-pyridyl)ethyl]-2-imidazoline, (42), using preparation method F

2-pyridyl-[7-(5-methoxy-2-methyl-benzofuranyl)]ketone (39)

To a stirred solution of 5-methoxy-2-methyl-benzofuran-7-carbonyl chloride (4.36 g, 19.40 mmol) in dry DMF (40 ml) was added 2-trimethylsilyl pyridine (2.94 ml, 19.40 mmol) and t-BuO$^-$K* (450 mg, 4.01 mmol). The reaction mixture was stirred at room temperature for 48 hours. The solvent was removed in vacuo and the residue dissolved in $CH_2Cl_2$ (100 ml) which was washed with water (3×40 ml), dried $MgSO_4$ and evaporated in vacuo yielding 5.43 g of a brown oil, >100%. Purification of the oil was done by chromatography together with the crude product from the next example.

2-pyridyl-[7-(5-methoxy-2-methyl-benzofuranyl)]ketone (39)

To a stirred solution of 5-methoxy-2-methyl-benzofuran-7-carboxylic acid anhydride (8.57 g, 21.73 mmol) in dry DMF (80 ml) was added 2-trimethylsilyl pyridine (1.64 g, 10.87 mmol) and t-BuO$^-$K* (225 mg, 2.0 mmol). The reaction mixture was stirred at 100° C. for 28 hours. The solvent was removed in vacuo and the residue dissolved in $CH_2Cl_2$ (180 ml) which was washed with water (1×60 ml), saturated $NaHCO_3$ (2×60 ml), dried $MgSO_4$ and evaporated in vacuo yielding 7.46 g of a brown crystallinic mass which was extracted with EtOH. Evaporation of the EtOH in vacuo left crude (39) 4.17 g as a brown oil. Purification of the combined oils by chromatography (5% AcOEt in $CH_2Cl_2$) yielded 3.95 g of (39) as a green oil which on standing crystallized into long needles but in solution turned dark/black.

The compound was stored in the dark or used immediately. $^1$H-NMR (400 MHz, d$_6$-DMSO) δ 8.68 (d, 1H), 8.11 (t, 1H), 8.03 (d, 1H), 7.71 (dd, 1H), 7.36 (d, 1H), 7.13 (d, 1H), 6.60 (s, 1H), 3.81 (s, 3H), 2.32 (s, 3H).

Ethyl 2-pyridyl-[7-(5-methoxy-2-methyl-benzofuranyl)]acrylate (40)

(40) was prepared in a way similar to the one described for (9). (40) was isolated as a light coloured oil, used without further purification.

TLC on silica gel (AcOEt/Heptane 1:1) revealed two spots which were supposed to be the Z and E isomer of (40).

$^1$H-NMR (80 MHz, CDCl$_3$) δ 8.60 (d, 1H), 7.79–7.09 (m, 3H), 7.29 and 7.03 (two s, 1H, Z and E methin), 6.89 (dd, 1H, H4 or H6 in Bf), 6.58 and 6.33 (two dd, 1H, H4 or H6 in Bf), 6.26 (s, 1H), 4.05 (dq, 2H), 3.75 and 3.65 (two s, 3H, OCH$_3$), 2.36 and 2.26 (two s, 3H).

Ethyl 3-[7-(5-methoxy-2-methyl-benzofuranyl)]-3-(2-pyridyl)-propionate (41)

(41) was prepared in a way similar to the one described for (6). (41) was purified by chromatography (AcOEt/Heptane 1:1) yielding (41) as a oil.

$^1$H-NMR (80 MHz, CDCl$_3$) δ 8.46 (d, 1H), 7.43 (t, 1H), 7.19 (s, 1H), 7.08 (d, 1H), 6.93 (d, 1H), 6.71 (d, 1H), 6.61 (d, 1H), 6.19 (s, 1H), 5.10 (dd, 1H, C$\underline{H}$—CH$_2$), 3.96 (q, 2H), 3.68 (s, 3H, OCH$_3$), 3.52 (dd, 1$\overline{H}$, CH—C$\underline{H}_2$), 2.98 (dd, 1H, CH—C$\underline{H}_2$), 2.35 (s, 3H), 1.06 (t, 3H).

2-[2-[7-(5-methoxy-2-methyl-benzofuranyl)]-2-(2-pyridyl)ethyl]-2-imidazoline (42)

(42) was prepared in a way similar to the one described for (7). (42) was purified by recrystallization (acetone).

Mp. 144°–145° C.

$^1$H-NMR (400 MHz, CDCl$_3$) δ 8.55 (d, 1H), 7,53 (dt, 1H), 7.27 (d, 1H), 7.10 (dt, 1H), 6.78 (d, 1H), 6.71 (d, 1H), 6.28 (s, 1H), 5.06 (dd, 1H, C$\underline{H}$—CH$_2$), 4.59 (bs, 1H, NH), 3.76 (s, 3H, OCH$_3$), 3.63 (bs, 2H, C$\underline{H}_2$—C$\underline{H}_2$), 3.43 (d$\overline{d}$, 1H, CH—C$\underline{H}_2$), 3.20 (bs, 2H), $\overline{3}$.03 ($\overline{dd}$, 1H, CH—C$\underline{H}_2$), 2.42 (s, 3H, CH$_3$).

| C$_{20}$H$_{21}$N$_3$O$_2$ | % C | % H | % N |
| --- | --- | --- | --- |
| Calculated | 71.61 | 6.32 | 12.53 |
| Found | 71.64 | 6.43 | 12.31 |

We claim:

1. A compound of the formula (I):

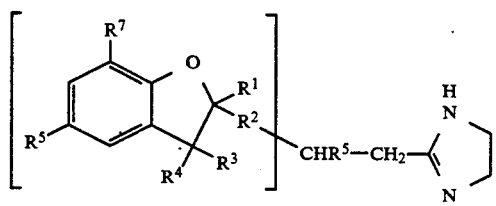

(I)

wherein R$^1$ is hydrogen, fluoro, chloro, bromo, C$_{1-4}$alkyl, C$_{1-4}$alkoxy or a bond to the side chain carrying the imidazoline ring; R$^2$ is hydrogen, fluoro, chloro, bromo, C$_{1-4}$alkyl, C$_{1-4}$alkoxy or R$^2$ together with R$^3$ represents an additional bond; R$^3$ is hydrogen, fluoro, chloro, bromo, C$_{1-4}$alkyl, C$_{1-4}$alkoxy, phenyl, or phenyl substituted by a substituent consisting of fluoro, chloro, C$_{1-4}$alkyl, and C$_{1-4}$alkoxy or R$^3$ together with R$^2$ represents an additional bond; R$^4$ is hydrogen, fluoro, chloro, bromo, C$_{1-4}$alkyl, C$_{1-4}$alkoxy, phenyl, or phenyl substituted by a substituent selected from the group consisting of fluoro, chloro, C$_{1-4}$alkyl, and C$_{1-4}$alkoxy; R$^5$ is hydrogen, fluoro, chloro, bromo, C$_{1-4}$alkyl, C$_{1-4}$alkoxy, hydroxy, phenyl, phenyl substituted by a substituent selected from the group consisting of methyl, methoxy, fluoro and chloro, or a bond to the side chain carrying the imidazoline ring; R$^6$ is phenyl, phenyl substituted by a substituent selected from the group consisting methyl, methoxy, fluoro and chloro, or 2-pyridyl, 3-pyridyl, or 4-pyridyl, or 2-pyridyl, 3-pyridyl, or 4-pyridyl, in which each pyridyl is substituted with a C$_{1-4}$alkyl group; and R$^7$ is hydrogen, fluoro, chloro, bromo, C$_{1-4}$alkyl, C$_{1-4}$alkoxy, hydroxy, phenyl, phenyl substituted by a substituent selected from the group consisting of methyl, methoxy, fluoro and chloro, or a bond to the side chain carrying the imidazoline ring or a pharmaceutically acceptable acid addition salt thereof.

2. The compound according to claim 1 in which R$^1$ is hydrogen, fluoro, chloro, bromo, C$_{1-4}$alkyl, or C$_{1-4}$alkoxy.

3. The compound according to claim 1 in which R$^2$ is hydrogen, fluoro, chloro, bromo, C$_{1-4}$alkyl, or C$_{1-4}$alkoxy.

4. The compound according to claim 1 in which R$^2$ together with R$^3$ represents an additional bond.

5. The compound according to claim 1 in which R$^3$ is hydrogen, fluoro, chloro, bromo, C$_{1-4}$alkyl, C$_{1-4}$alkoxy, phenyl, or phenyl substituted by a substituent selected from the group consisting of fluoro, chloro, C$_{1-4}$alkyl, and C$_{1-4}$alkoxy.

6. The compound according to claim 1 in which R$^3$ is phenyl substituted by a methyl group.

7. The compound according to claim 1 in which R$^3$ is phenyl substituted by a methoxy group.

8. The compound according to claim 1 in which R$^4$ is hydrogen, fluoro, chloro, bromo, C$_{1-4}$alkyl, C$_{1-4}$alkoxy, phenyl, or phenyl substituted by a substituent selected from the group consisting of fluoro, chloro, C$_{1-4}$alkyl, and C$_{1-4}$alkoxy.

9. The compound according to claim 1 in which R$^4$ is phenyl substituted by a methyl group.

10. The compound according to claim 1 in which R$^4$ is phenyl substituted by a methoxy group.

11. The compound according to claim 1 in which R$^5$ is hydrogen, fluoro, chloro, bromo, C$_{1-4}$alkyl, C$_{1-4}$alkoxy, hydroxy, phenyl, or phenyl substituted by a substituent selected from the group consisting of fluoro, chloro, methyl, and methoxy.

12. The compound according to claim 1 in which each pyridyl is substituted with a methyl group.

13. The compound according to claim 1 in which R$^7$ is hydrogen, fluoro, chloro, bromo, C$_{1-4}$alkyl, C$_{1-4}$alkoxy, hydroxy, phenyl, or phenyl substituted by a substituent selected from the group consisting of fluoro, chloro, methyl, and methoxy.

14. The compound according to claim 1 in which R$^5$ and R$^7$ are independently hydrogen, fluoro, chloro, bromo, C$_{1-4}$alkyl, C$_{1-4}$alkoxy, hydroxy, phenyl, or phenyl substituted by a substituent selected from the group consisting of fluoro, chloro, methyl, and methoxy.

15. The compound according to claim 1 in which R$^1$ is hydrogen, fluoro, chloro, bromo, C$_{1-4}$alkyl, or C$_{1-4}$alkoxy and R$^7$ is hydrogen, fluoro, chloro, bromo, C$_{1-4}$alkyl, C$_{1-4}$alkoxy, hydroxy, phenyl, or phenyl substituted by a substituent selected from the group consisting of fluoro, chloro, methyl, and methoxy.

16. The compound according to claim 1 in which $R^1$ is hydrogen, fluoro, chloro, bromo, $C_{1-4}$alkyl or $C_{1-4}$alkoxy, and $R^5$ is hydrogen, fluoro, chloro, bromo, $C_{1-4}$alkyl or $C_{1-4}$alkoxy, hydroxy, phenyl, or phenyl substituted by a substituent selected from the group consisting of fluoro, chloro, methyl, and methoxy.

17. A pharmaceutical composition for the treatment of type 2 diabetes comprising a compound of the formula (I):

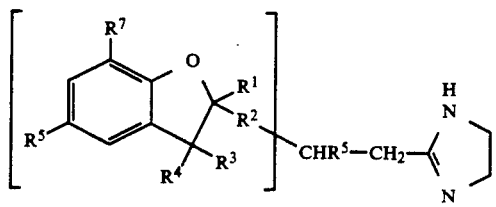

wherein $R^1$ is hydrogen, fluoro, chloro, bromo. $C_{1-4}$alkyl, $C_{1-4}$alkoxy or a bond to the side chain carrying the imidazoline ring; $R^1$ is hydrogen, fluoro, chloro, bromo, $C_{1-4}$alkyl, $C_{1-4}$alkoxy or $R^2$ together with $R^3$ represents an additional bond; $R^3$ is hydrogen, fluoro, chloro, bromo, $C_{1-4}$alkyl, $C_{1-4}$alkoxy, phenyl, or phenyl substituted by a substituent selected from the group consisting of fluoro, chloro, $C_{1-4}$alkyl, $C_{1-4}$alkoxy or $R^3$ together with $R^2$ represents an additional bond; $R^4$ is hydrogen fluoro, chloro, bromo, $C_{1-4}$alkyl, $C_{1-4}$alkoxy, phenyl, or phenyl substituted by a substituent selected from the group consisting of fluoro, chloro, $C_{1-4}$alkyl, $C_{1-4}$alkoxy; $R^5$ is hydrogen, fluoro, chloro, bromo, $C_{1-4}$alkyl, $C_{1-4}$alkoxy, phenyl, hydroxy, or a bond to the side chain carrying the imidazoline ring; $R^6$ is phenyl, 2-pyridyl, 3-pyridyl, or 4-pyridyl; and $R^7$ is hydrogen, fluoro, chloro, bromo, $C_{1-4}$alkyl, $C_{1-4}$alkoxy, phenyl, hydroxy, or a bond to the side chain carrying the imidazoline ring or a pharmaceutically acceptable acid addition salt thereof.

18. A method for treating type 2 diabetes in a mammal comprising administering an amount of a compound of the formula (I):

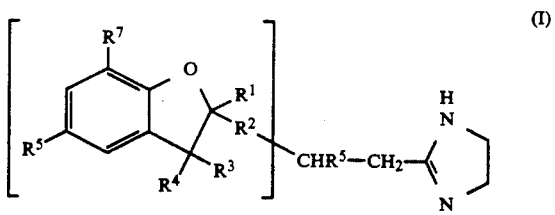

wherein $R^1$ is hydrogen, fluoro, chloro, bromo, $C_{1-4}$alkyl, $C_{1-4}$alkoxy or a bond to the side chain carrying the imidazoline ring; $R^2$ is hydrogen, fluoro, chloro, bromo, $C_{1-4}$alkyl, $C_{1-4}$alkoxy or $R^2$ together with $R^3$ represents an additional bond; $R^3$ is hydrogen, fluoro, chloro, bromo, $C_{1-4}$alkyl, $C_{1-4}$alkoxy, phenyl, or phenyl substituted by a substituent selected from the group consisting of fluoro, chloro, $C_{1-4}$alkyl, and $C_{1-4}$alkoxy or $R^3$ together with $R^2$ represents an additional bond; $R^4$ is hydrogen, fluoro, chloro, bromo, $C_{1-4}$alkyl, $C_{1-4}$alkoxy, phenyl, or phenyl substituted by a substituent selected from the group consisting of fluoro, chloro, $C_{1-4}$alkyl, and $C_{1-4}$alkoxy; $R^5$ is hydrogen, fluoro, chloro, bromo, $C_{1-4}$alkyl, $C_{1-4}$alkoxy, hydroxy, phenyl, phenyl substituted by a substituent selected from the group consisting of methyl, methoxy, fluoro and chloro, or a bond to the side chain carrying the imidazoline ring; $R^6$ is phenyl, phenyl substituted by a substituent selected from the group consisting of methyl, methoxy, fluoro and chloro, or 2-pyridyl, 3-pyridyl, or 4-pyridyl, or 2-pyridyl, 3-pyridyl, or 4-pyridyl, in which each pyridyl is substituted with a $C_{1-4}$alkyl group; and $R^7$ is hydrogen, fluoro, chloro, bromo, $C_{1-4}$alkyl, $C_{1-4}$alkoxy, hydroxy, phenyl, phenyl substituted by a substituent selected from the group consisting of methyl, methoxy, fluoro and chloro, or a bond to the side chain carrying the imidazoline ring or a pharmaceutically acceptable acid addition salt thereof, effective to decrease the blood glucose level of the mammal to a normal level.

* * * * *